(12) United States Patent
Spiegel et al.

(10) Patent No.: US 8,291,768 B2
(45) Date of Patent: Oct. 23, 2012

(54) PRESSURE MEASURING SYRINGE

(75) Inventors: Joan E. Spiegel, Boston, MA (US); Alexander H. Slocum, Cambridge, MA (US); Adrienne Watral, Lynnwood, WA (US); Samuel Duffley, Billerica, MA (US)

(73) Assignees: Beth Israel Deaconess Medical Center, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/688,599

(22) Filed: Jan. 15, 2010

(65) Prior Publication Data

US 2010/0179488 A1 Jul. 15, 2010

Related U.S. Application Data

(60) Provisional application No. 61/144,956, filed on Jan. 15, 2009.

(51) Int. Cl.
*G01L 7/00* (2006.01)
*A61M 5/175* (2006.01)

(52) U.S. Cl. .......................... 73/700; 604/121; 604/227
(58) Field of Classification Search .............. 73/700–756
See application file for complete search history.

(56) References Cited

U.S. PATENT DOCUMENTS

| 4,064,879 A | 12/1977 | Leibinsohn |
| 4,159,722 A | 7/1979 | Walker |
| D260,814 S | 9/1981 | Goldhardt et al. |
| 4,346,708 A | 8/1982 | LeVeen et al. |
| 4,403,988 A | 9/1983 | Binard et al. |
| 4,617,015 A | 10/1986 | Foltz |
| 4,759,750 A | 7/1988 | DeVries et al. |
| 4,924,862 A | 5/1990 | Levinson |
| 5,235,973 A | 8/1993 | Levinson |
| 5,487,383 A | 1/1996 | Levinson |
| RE35,531 E | 6/1997 | Callaghan et al. |
| 5,722,955 A | 3/1998 | Racz |
| 6,070,581 A | 6/2000 | Augustine et al. |
| 6,086,569 A * | 7/2000 | Schweizer ................ 604/227 |
| 6,631,720 B1 | 10/2003 | Brain |
| 7,018,359 B2 | 3/2006 | Igarashi et al. |

(Continued)

FOREIGN PATENT DOCUMENTS

EP  1 062 964  12/2000

OTHER PUBLICATIONS

Bremer et al., "Endotracheal Tube Pressure Monitor," BME 201, Dept. of Biomedical Engineering, University of Wisconsin-Madison, May 7, 2008.

*Primary Examiner* — Andre Allen
(74) *Attorney, Agent, or Firm* — Weingarten, Schurgin, Gagnebin & Lebovici LLP

(57) ABSTRACT

A syringe having an internal pressure gauge comprises a syringe barrel; a piston within the barrel; a spring coupled to the piston at a first position of the spring, the spring having a second portion that is movable in response to fluid pressure within a syringe cavity; and a pressure gauge having an indicator correlated to a plurality of positions of the second portion of the spring to indicate a pressure of a fluid. The spring can be a bellows. The fluid chamber can be in fluid communication with a cuff of an inflatable medical device, such as an endotracheal tube, such that the measured pressure comprises the fluid pressure within the cuff.

50 Claims, 11 Drawing Sheets

U.S. PATENT DOCUMENTS

| | | |
|---|---|---|
| 7,273,053 B2 | 9/2007 | Zocca et al. |
| 7,331,346 B2 | 2/2008 | Zocca et al. |
| 7,351,223 B2 | 4/2008 | Call |
| 7,383,736 B2 | 6/2008 | Esnouf |
| 2007/0068532 A1 | 3/2007 | Le et al. |
| 2007/0113857 A1 | 5/2007 | Weiss et al. |
| 2007/0149922 A1 | 6/2007 | Schneider et al. |
| 2007/0163599 A1 | 7/2007 | Mijers |
| 2007/0213594 A1 | 9/2007 | Nguyen |
| 2009/0159085 A1 | 6/2009 | Sleva |
| 2009/0194113 A1 | 8/2009 | Chen et al. |
| 2009/0227947 A1 | 9/2009 | Caclin |
| 2009/0281489 A1 | 11/2009 | Lampropoulos et al. |
| 2010/0078030 A1 | 4/2010 | Colburn |
| 2010/0116360 A1 * | 5/2010 | Kanner et al. ............... 137/383 |

* cited by examiner

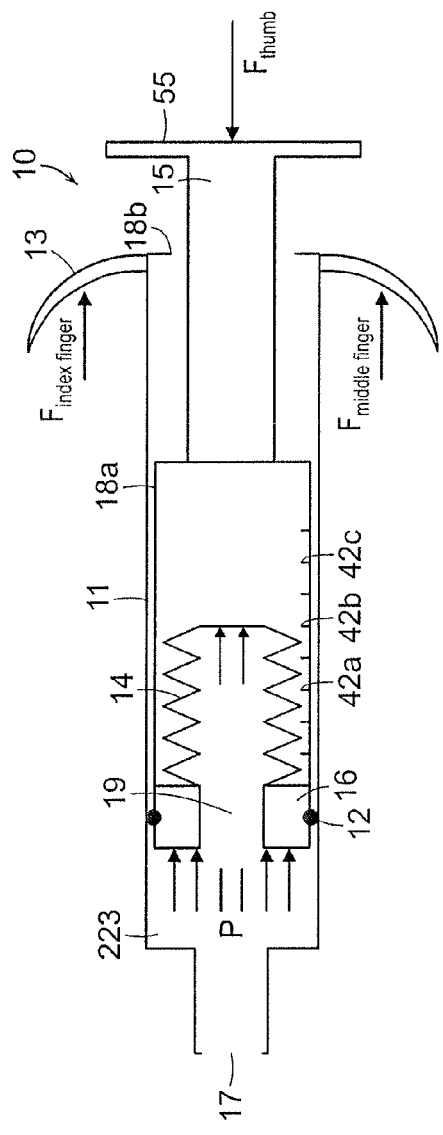
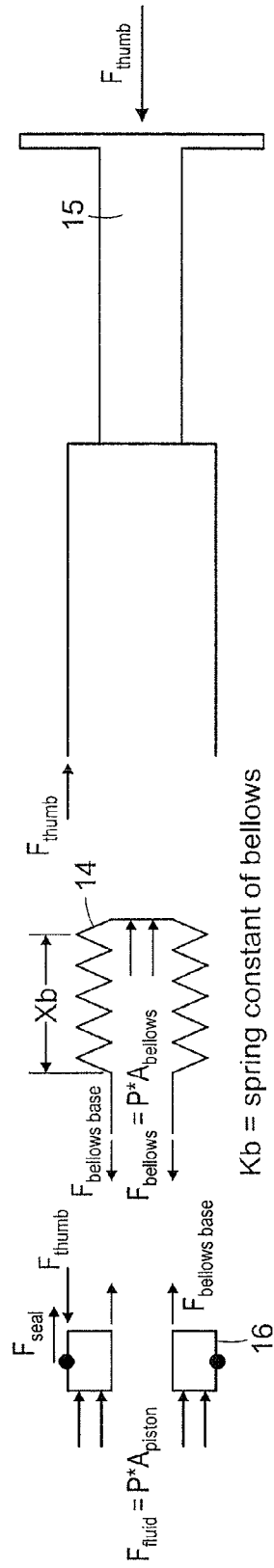
FIG. 2A
FIG. 2B

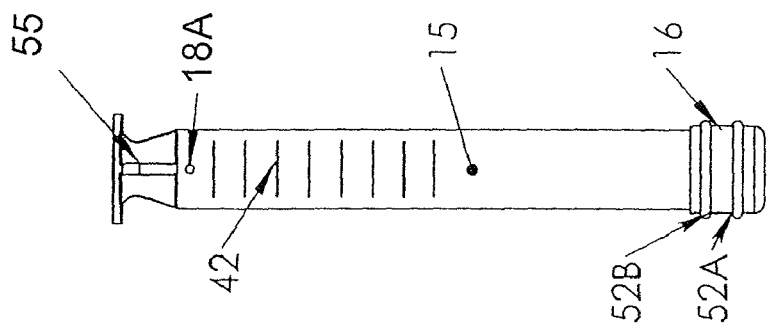
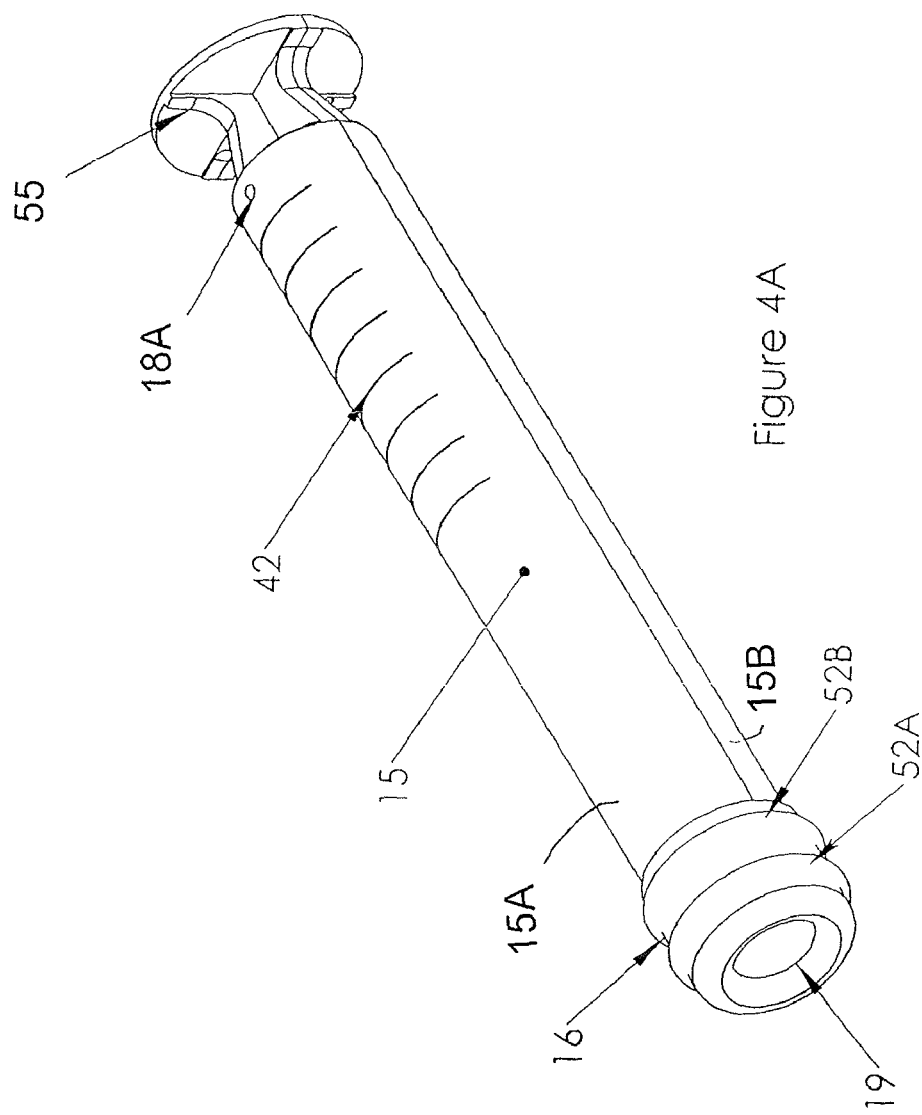

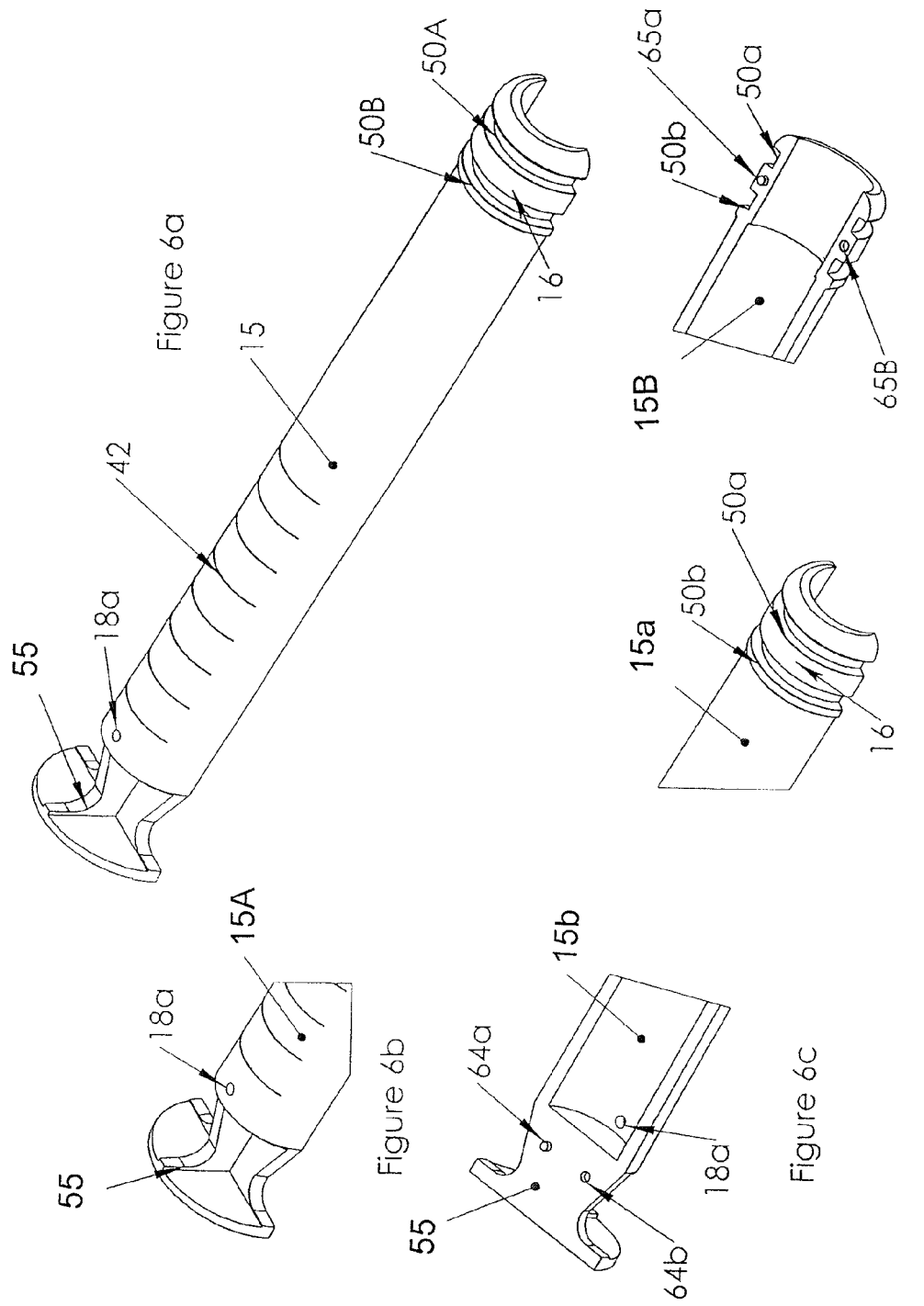

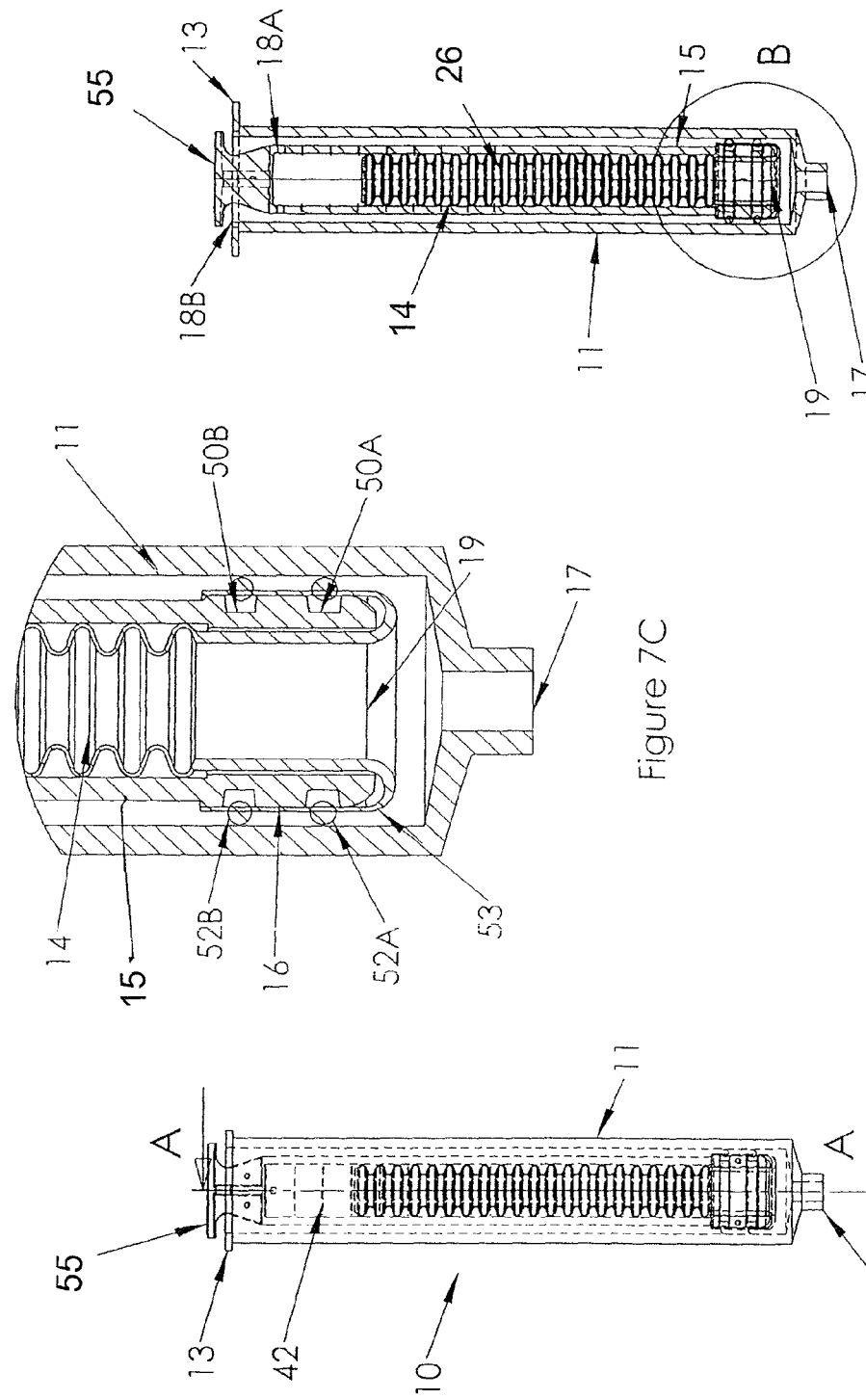

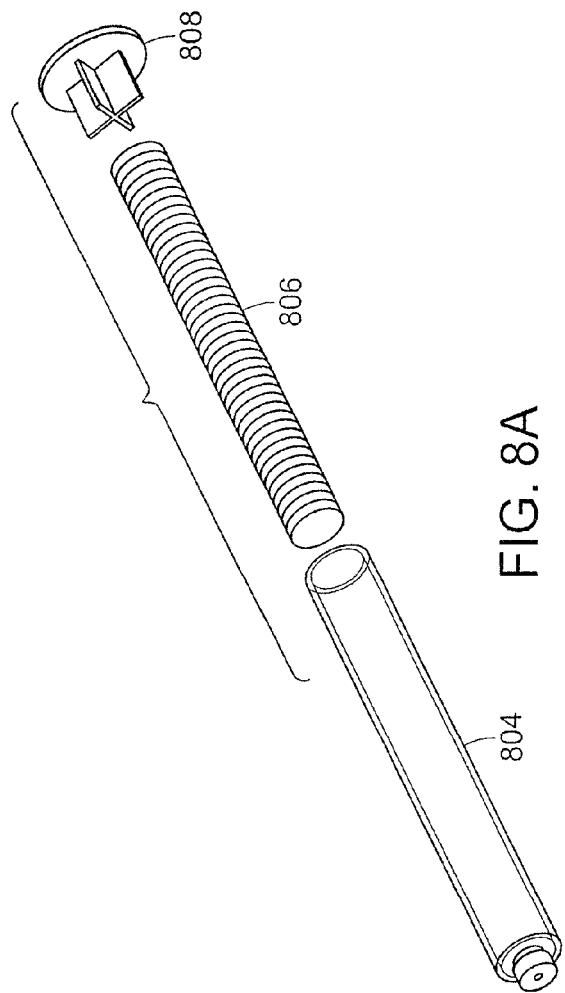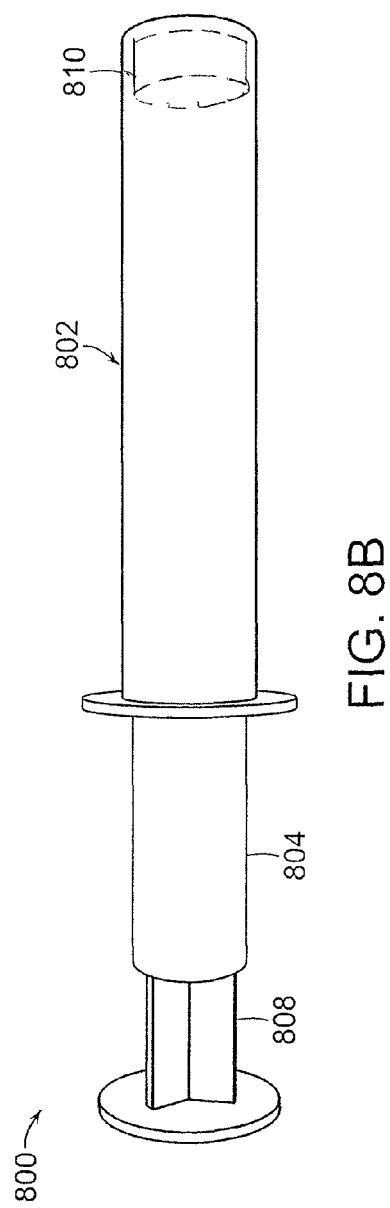

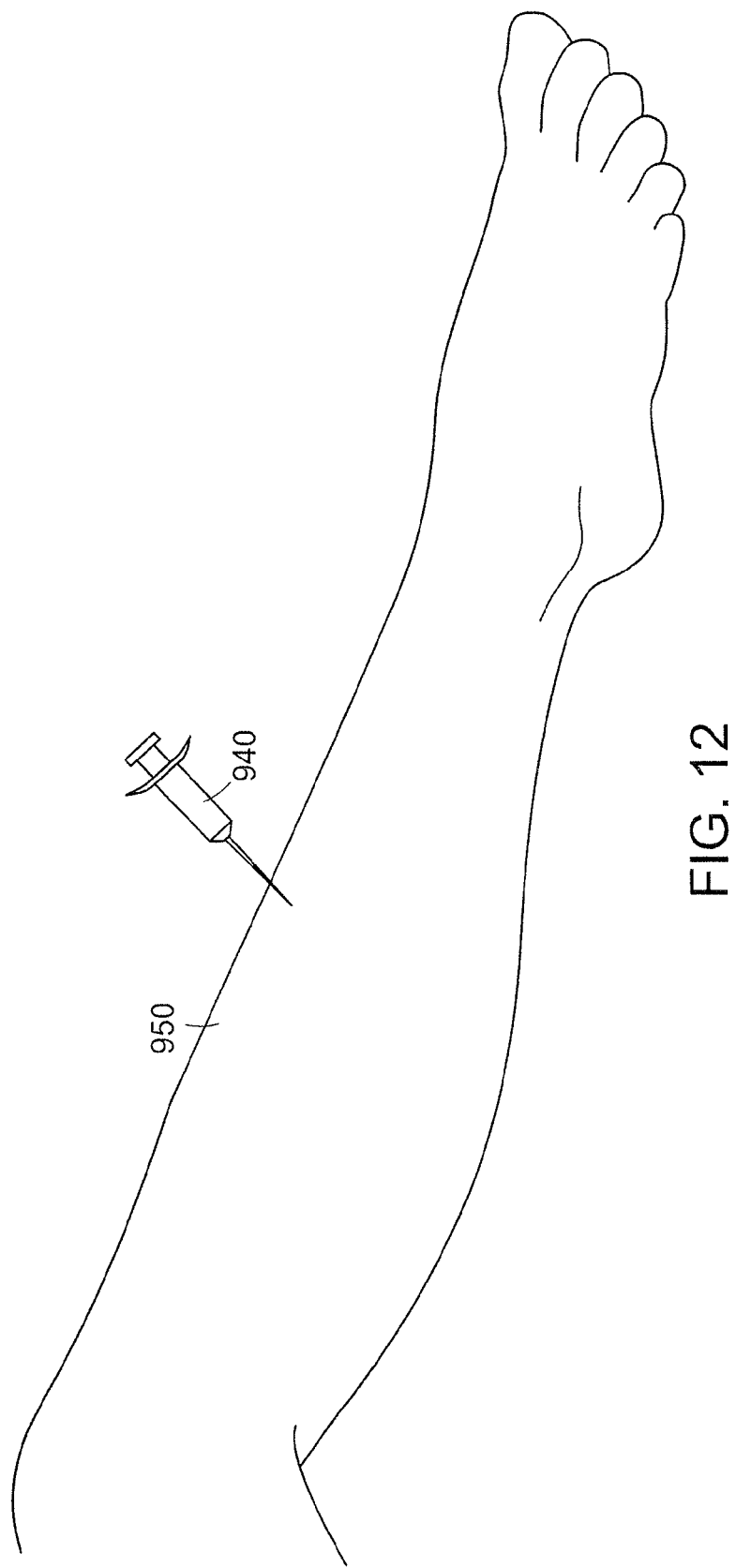

PRESSURE MEASURING SYRINGE

CROSS-REFERENCE TO RELATED APPLICATIONS

This application claims the benefit of U.S. Provisional Application No. 61/144,956, filed Jan. 15, 2009.

STATEMENT REGARDING FEDERALLY SPONSORED RESEARCH

This invention was made with government support under grant number W81XWH-07-2-0011, awarded by the Army MRMC. The Government has certain rights in this invention.

BACKGROUND OF THE INVENTION

An endotracheal tube (ETT) is commonly used in medical procedures, such as during anesthesia, intensive care, and emergency care, to provide an open airway to the patient's lungs, as may be required, for example, for mechanical ventilation. The ETT is inserted into the patient's trachea, in a process known as intubation, and typically a balloon-like cuff near the distal end of the tube is inflated to secure the tube within the trachea and prevent leaks around the tube.

When intubating a patient, it is important to avoid over-inflation of the cuff, since excessive cuff pressure against the tracheal wall can cause mucosal ischemia, and the subsequent pressure necrosis can lead to tracheal stenosis. Other catastrophic complications of an over-inflated cuff include mucosal ulceration, perforation, scarring and rupture of the trachea, and fistula.

It is also critical that the cuff is sufficiently inflated to adequately seal against the tracheal wall. Consequences of an under-inflated cuff include not only air leakage around the tube, but also serious complications such as silent aspiration of secretions and other foreign material, which can lead to pneumonia and other serious conditions.

Therefore, in order to avoid these myriad problems relating to both over-inflation and under-inflation of an ETT cuff, it is imperative that the cuff is inflated to a pressure that falls within a narrow range of acceptable cuff pressures. Furthermore, unsafe cuff pressures can develop in an intubated patient over time. Leaks in the cuff or elsewhere in the ETT can result in a gradual pressure loss, and absorption by the cuff of certain gases, such as nitrous oxide, can actually increase cuff pressure during intubation. Changes in patient conditions over prolonged period may also require adjustments to the cuff pressure. Therefore, it is important that the cuff pressure is routinely monitored and maintained within the acceptable pressure range.

Differences in anatomy and opposing tracheal pressures amongst individuals render the volume of the fluid within the cuff an inaccurate proxy for cuff pressure, even in identically-sized cuffs. Thus, the cuff pressure cannot be reliably controlled by simply maintaining a pre-determined volume of air within the cuff.

Presently, the most common technique used by clinicians for monitoring cuff pressure is to estimate the pressure by finger palpation of the syringe used to inflate the cuff, or in some cases, finger palpation of a pilot balloon external to the patient and in fluid communication with the cuff. This technique has been demonstrated to be highly inaccurate. Syringe employed to inflate the cuff have been adopted to measure pressure but have failed to provide the sensitivity and range for reliable cuff pressure measurement. Another approach is to directly measure the cuff pressure by attaching a separate manometer to the inlet valve of the cuff. However, manometers are bulky, expensive devices that are typically not used nor readily available at the point-of-care. Furthermore, these devices are not always accurate, since many pressure gauges add compressible volume which can affect measurement and can even negatively effect cuff pressure as a result of the measurement.

SUMMARY OF THE INVENTION

The present invention relates to a pressure measuring syringe. A preferred embodiment utilizes a spring mounted to a syringe plunger that is displaced by the fluid pressure in the distal chamber of the syringe. A preferred embodiment mounts a spring in the form of a flexible diaphragm or bellows to the plunger of the syringe that reduces the friction of the system to provide a more accurate measurement of fluid pressure, particularly at lower pressures.

In order to ensure safety of intubated patients, a preferred embodiment of the invention provides for the measurement of endotracheal tube cuff pressure that is maintained within a narrow band of pressures. The present invention further provides an inflation device for inflating the cuff within a selected range, preferably between 15 and 35 cm $H_2O$, and even more preferably between about 20 and 30 cm $H_2O$. A preferred embodiment of the invention provides a syringe having a pressure gauge that indicates at least an upper pressure level and a lower pressure level indicative of over-inflation and under-inflation of an endotracheal cuff, respectively. For certain applications, such as the intubation of pediatric patients it can be desirable to measure lower pressures in a range of 5 to 20 cm $H_2O$.

According to one aspect of the present invention, a syringe having an internal pressure gauge comprises a barrel having an aperture at a tip end and an opening at an opposed end; a plunger or piston arranged within the barrel and forming a seal against an internal wall of the barrel to define a fluid chamber proximate the plunger. A spring, flexible diaphragm or bellows arranged within the barrel is axially movable within the piston. The spring, flexible diaphragm or bellows operates as a moveable pressure indicator and can be mounted at a first end to the plunger and is free to move at a second end. The pressure indicator, such as a spring, can be calibrated to provide a resistance force against the axial movement that is indicative of a pressure within the fluid chamber. Visual indicia are used to indicate the pressure within the fluid chamber based on the relative position of the spring, the visual indicia indicating gas pressures within a range between a lower pressure limit and an upper pressure limit, or approximately from 5 to 35 cm $H_2O$. The fluid chamber can be in fluid communication with a cuff of an endotracheal tube, such that the measured pressure comprises the fluid pressure within the cuff. As the end of the spring or bellows is free to move without any substantial friction against the inner tubular wall of the plunger, it can more accurately reflect the gas pressure in the syringe chamber. The proximal end or second portion of the spring is thus mechanically decoupled from the inner wall of the plunger and consequently operates without the use of a seal. The distal end of the spring (or first portions) is coupled to the plunger in such a way that a seal is formed between the outer peripheral surface of a portion of the plunger and inner wall of the syringe barrel so that displacement of the plunger will displace fluid through the distal opening of the syringe.

In certain embodiments, the visual indicia indicate gas pressures within a range of approximately 20 to 30 cm $H_2O$. The visual indicia can be located on the piston and can comprise, for example, graduated markings and/or color coded markings. A preferred embodiment of the invention includes a syringe having a volume of 10 cc. However, for smaller patients, such as children a 5 cc syringe can be preferred. Thus, preferred embodiments of the syringe will have a displaceable value in a range of 2 to 20 cc.

According to another aspect, a method of measuring the pressure within a cuff of an endotracheal tube comprises providing a syringe in accordance with the invention in fluid communication with the cuff, actuating the syringe by depressing the plunger relative to the barrel, and detecting the visual indicia to measure the pressure inside the cuff. For circumstances involving longer term use, such as with a ventilator, it is desirable to monitor the pressure in the cuff, however, in certain cases it is not desirable to maintain a syringe adjacent to the patient's mouth. The syringe can be marked with a reattachment location for the plunger whereby the user can connect the syringe to the port or inlet valve whereby opening the valve will not significantly alter the pressure existing in the cuff and enable the measurement of the current cuff pressure. This enables periodic reconnection and measurement of cuff pressure without the need to completely reinflate the cuff. Preferably, the seal between the plunger and the outer wall of the syringe is sufficient to hold the plunger in place after the user releases pressure, thereby permitting an ongoing measurement of pressure.

BRIEF DESCRIPTION OF THE DRAWINGS

FIG. 2A is side cross section schematic of one embodiment of the present invention illustrating a plunger pushing on a piston which has a hole in it to allow the resulting pressure in the syringe barrel to elastically deform a bellows;

FIG. 2B is free body diagram of the components of FIG. 2A;

FIG. 4A is an isometric view of the preferred embodiment of the plunger assembly;

FIG. 4B is side view of the preferred embodiment of the plunger assembly;

FIG. 6A is an isometric view of the preferred embodiment of the plunger;

FIG. 6B is a top side close up isometric view of the end of the preferred embodiment of the syringe assembly where the caregiver thumb pushes on it;

FIG. 6C is a bottom side close up isometric view of the end of the preferred embodiment of the syringe assembly where the caregiver thumb pushes on it;

FIG. 6D is a top side close up isometric view of the piston end of the preferred embodiment of the syringe;

FIG. 6E is a bottom side close up isometric view of the piston end of the preferred embodiment of the syringe;

FIG. 7A is a hidden line side view of the preferred embodiment of the syringe assembly;

FIG. 7B is a cross section side view of the preferred embodiment of the syringe assembly;

FIG. 7C is a close up cross section view of the tip region of the preferred embodiment of the syringe assembly;

FIGS. 8A and 8B illustrate an embodiment of a pressure measuring syringe having a bellows in the syringe plunger;

FIG. 12 illustrates a pressure-measuring syringe used in a pressure-sensitive medical procedure on a patient.

DETAILED DESCRIPTION OF THE INVENTION

This application claims the benefit of U.S. Provisional Application No. 61/144,956, filed Jan. 15, 2009, the entire teachings of which are incorporated herein by reference.

Figure 1:
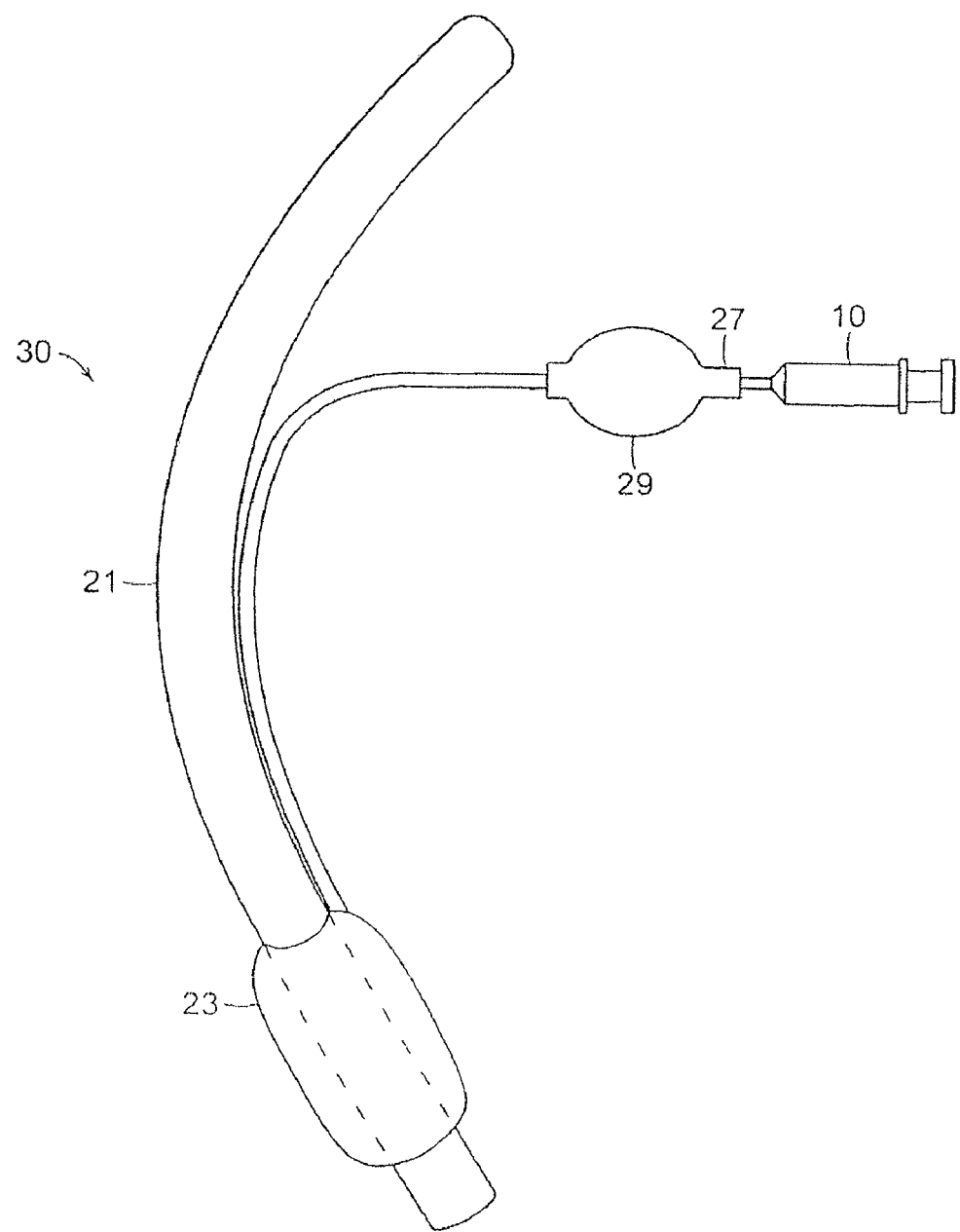
FIG. 1 illustrates an endotracheal tube assembly and a syringe for inflating a cuff.

The invention comprises a syringe 10 having an internal pressure gauge, and can be used in connection with an endotracheal tube assembly 20, such as is schematically illustrated in FIG. 1. The endotracheal tube assembly 20 includes an elongated tubular member 21 that can be inserted into the windpipe (trachea) of a patient to provide an open air passageway to and from the patient's lung(s). Typically, the tube assembly 20 comprises an inflatable cuff 23 near the distal end of the tubular member 23. The cuff 23 is generally in an un-inflated state when the assembly 20 is introduced into the patient's trachea. The cuffs currently in use are referred to as high volume and low pressure, such as those manufactured by Portex, Ltd., Hythe, U.K. The cuff volume can be in the range of 15 to 20 cc when fully inflated, however, in most adult patients the inflated volume is about 6 cc. Inflation volumes are generally in a range of 4-10 cc. When the assembly 20 is properly positioned within the trachea, the cuff 23 is inflated by introducing a fluid, such as air, into the cuff 23 through a small fluid tube 25 extending from the cuff 23 to an inlet valve 27 located outside the patient. The cuff 23 is inflated to seal the cuff 23 against the patient's trachea. The tube assembly 20 can also include an inflatable pilot balloon 29 that is located external to the patient and is in fluid communication with the cuff 23 to provide an approximation of the level of cuff inflation and of the fluid pressure inside the cuff 23.

The syringe 10 is inserted into a port of the inlet valve 27 of the tube assembly 20, and can be used to inflate and/or deflate the cuff 23, as is known in the art. According to one aspect of the present invention, the syringe 10 includes an internal pressure measurement device, as described below, that can be advantageously used to visually monitor the fluid pressure within the cuff 23. Cuff pressure is a significant parameter in intubated patients, whether they are in the operating room or the intensive care unit, as a cuff that is underinflated (i.e. cuff pressure too low) will not properly seal against the tracheal wall, resulting in air leaks around the tube 21, as well as the flow of secretions and other foreign material into the lungs. It is also known that a cuff that is overinflated (i.e. cuff pressure too high) can impede mucosal blood flow in the trachea, and predispose the patient to ischemic, occasionally catastrophic, complications. Endotracheal tube cuff pressure in most cases should not exceed approximately 35 cm $H_2O$, and should not be below about 15 cm $H_2O$. Ideally, the cuff pressure should be maintained at a level between about 20 and 30 cm $H_2O$.

The syringe 10 of the present invention comprises an internal pressure gauge that can measure the internal pressure of an inflatable medical device, such as the cuff of an endotracheal tube, to which the syringe is connected, and which provides a simple, visual indication of whether the cuff is underinflated, properly inflated, or overinflated.

According to one aspect, the pressure measuring device is well-incorporated into existing syringe designs. Integrating the pressure measurement apparatus into the syringe provides a product that is intuitive to doctors and other health care professionals, and is easy to incorporate into existing intubation techniques.

A preferred embodiment of the invention includes an internal spring device that is actuated by air pressure in the syringe. As the pressure in the syringe increases, the displacement of the spring device moves an indicator along the length of the syringe plunger in proportion to the pressure-induced force on it according to Hooke's Law, force being equal to the spring constant times the displacement. Advantages of the internal air spring are that the design is relatively simple and entails few changes to existing syringe designs. The analysis of the pressure indicator is relatively straightforward and predictable.

According to one aspect of the invention, a syringe includes a pressure sensor that comprises a seal and a spring. The seal maintains the pressure differential between the pressure in the cuff and atmospheric pressure, and that pressure differential drives the deflection of a spring, providing information to the user about the magnitude of the pressure. The spring can be, for example, a coiled spring with a diaphragm covering. A soft rubber bellows can be used to combine the spring action and the seal into one simple mechanism.

FIGS. 2A and 2B are schematic illustrations of one embodiment of the present invention. As shown in FIGS. 2A and 2B, a syringe 10 is similar to a conventional syringe in both design and operation. A plunger 15 reciprocates within an outer shell 11. A piston end 16, attached to the plunger 15, provides a fluid-tight seal 12 against the outer barrel 11, and defines a fluid chamber 223 proximate the tip of the syringe 10. As the plunger 15 and piston end 16 move within the outer barrel 11, pressurized fluid (e.g., air or liquid) flows through an opening 17 in the syringe tip, which can include a connection element (such as a Luer-lok portion) for forming a fluid-tight connection with an external fluid conduit. In some embodiments, the syringe 10 can be connected to an inflatable medical cuff, such as the endotracheal tube cuff shown in FIG. 1.

Figure 3A:
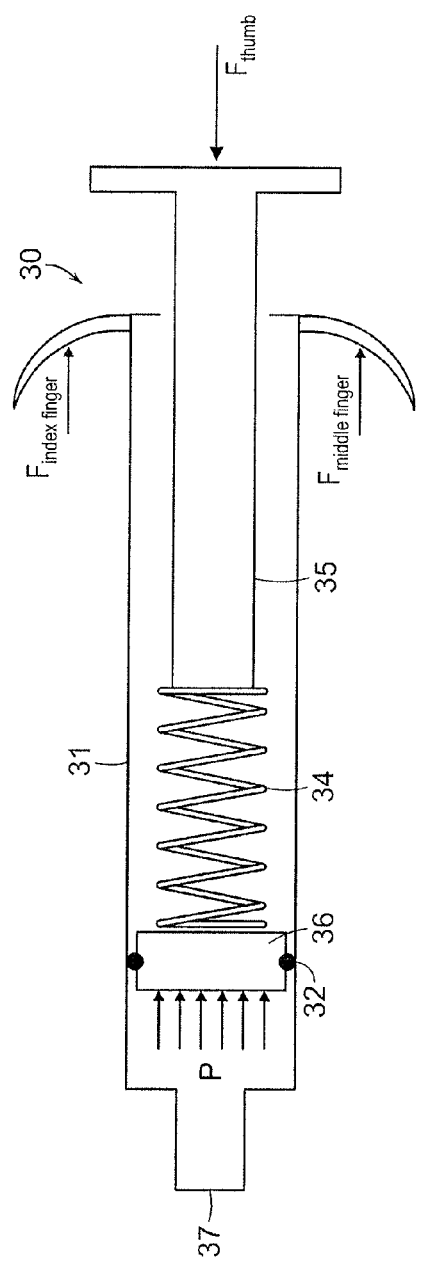
FIG. 3A is side cross section schematic of a plunger syringe that pushes on a spring which pushes on a piston.

In the embodiment of FIG. 3A, a pair of flanges 13 are located on the outer shell 11. In a typical operation of the syringe 10, a user braces his or her fingers (e.g., index and middle fingers) against the flanges 13 while applying thumb force against the end cap 55 of the piston 15 in order to depress the plunger 15 and force fluid out from the tip 17.

The syringe 10 further includes an internal pressure sensor in the form of a bellows 14. In this embodiment, the bellows 14 is secured to the piston end 16. The piston end 16 includes a central opening 19 to provide fluid communication between the fluid chamber 223 and the interior of the bellows 14. The bellows 14 provides a seal between the fluid pressure inside and outside of the fluid chamber 223, and further functions as a spring, where the displacement of the spring is driven by the pressure differential between the fluid inside and outside of the bellows 14. In the embodiment of FIG. 2A, the fluid pressure inside the bellows 14 equilibrates with the pressure, P, inside the fluid chamber 223. The fluid pressure outside the bellows 14 equilibrates with atmospheric pressure, as both the interior of the plunger 15 and the outer barrel 11 are vented to the atmosphere via vent openings 18a and 18b, respectively.

As is illustrated in FIG. 2B, the displacement of the bellows, $X_b$, is proportional to the pressure-induced bellows force, $F_{bellows}$, and the bellows spring constant, $K_b$. Thus, the syringe 10 can be calibrated so that the displacement of the bellows 14 provides an accurate measurement of the fluid pressure, P, inside the fluid chamber 223 over any pressure range of interest. The plunger 15 can include visual indicators, such as graduated markings 42a, 42b, 42c, indicative of a numerical pressure value measured by the displacement of the bellows 14. Markings 42a, 42b, 42c can also be provided to indicate a safe range of operating pressures for a particular application. In the case where the syringe 10 is attached to an inflatable medical cuff, such as a cuff of an endotracheal tube, for example, the markings 42b and 42c can provide a clear visual indication of the respective lower and upper limits for safe cuff inflation pressure.

As the plunger 15 is depressed, the thumb force travels down the plunger and instead of pushing on a spring, it pushes directly on the piston end of the plunger 16, which pushes back with the same force $F_{thumb}$. The piston end 16 also has forces on it of $F_{seal}$ due to the sliding friction between the seal 12 and the outer barrel 11, and the force $F_{fluid}$ which is the product of the fluid pressure P and the area A of the piston, where in this case, the area A is a function of the piston outer diameter and the diameter of the inner hole 19.

A small amount of the fluid also flows through hole 19 and into the bellows 14 causing the bellows to elastically expand to a length $X_b$. The product of the effective cross sectional area $A_{bellows}$ and the pressure P is the force $F_{bellows\ base}$ which acts directly on the piston. However, $F_{bellows\ base}$ will be equal to the product of the bellows spring constant $K_b$ and the axial expansion of the bellows ($X_b$ minus the free length of the bellows). Thus, by observing the change in length of the bellows, the caregiver has a direct measurement of the pressure P being delivered to the cuff, and this measurement is not affected by the unknown seal friction force.

In this embodiment, the plunger and outer barrel have vents 18a and 18b respectively, so the outside of the bellows is subject to the ambient atmosphere. Hence, an accurate pressure reading can be made regardless of altitude or barometric pressure.

Preferably, both the barrel 11 and the plunger 15 are comprised of transparent materials, so that the bellows is readily visible to the operator. The spring constant $k_{bellows}$ can be calibrated so the pressure P can be accurately determined as described above. When the syringe outlet 17 is connected to an external device, such as an inflatable medical cuff 23 (FIG. 1), the inside chamber of the bellows 14 is in direct fluid communication with cuff 23 (i.e. during cuff inflation/deflation or during a cuff monitoring procedure), and the pressure, P, inside the bellows 14 is equal to the pressure within the cuff. Therefore, the axial expansion of the bellows can be used to directly measure the fluid pressure within the cuff.

Modern ETT cuffs are generally inflated to relatively low pressures, and as previously mentioned, the safe range of cuff pressures is within a narrow band of pressures between about 15 and 35 cm $H_2O$ or more generally between 15 cm $H_2O$ and 50 cm $H_2O$. In some cases, such as tubes for pediatric patients, the cuff pressure can be between 0 and about 15 cm $H_2O$, and frequently less than about 10 cm $H_2O$. Thus, ideally the syringe should be calibrated to provide accurate measurements of fluid pressures within and immediately surrounding the particular range of safe cuff pressure(s) for the particular cuff(s) of interest. In the embodiment of FIG. 2A, the plunger includes graduated markings 42 along its length that are indicative of the fluid pressure P in the syringe. In addition, the markings 42 can include colors to assist the clinician in determining whether the cuff inflation pressure is within the "safe" range. For example, portion of the plunger indicated at 42a can have a red coloration to indicate that the cuff pressure is too low (e.g. <15 cm $H_2O$), the portion indicated at 42b can be white to indicate cuff pressures within the "safe" range (e.g. 15-35 cm $H_2O$), and the portion indicated at 42c can have a darker red coloration to indicate that the cuff is inflated at too high a pressure (e.g. >35 cm $H_2O$). It will be understood that numerous variations of this color-coding scheme can be implemented in accordance with the principles of present invention. Further, a visual indicator can be provided on the bellows, such that as the bellows expands and contracts, the indicator moves longitudinally relative to the plunger to indicate fluid pressure.

In particular embodiments, the syringe has a plurality of markers indicating a pressure range of at least 5 to 35 cm $H_2O$, or 10 to 35 cm $H_2O$, or in some embodiments, 10 to 20 cm $H_2O$. Other pressure ranges are contemplated by the invention.

Figure 3B:
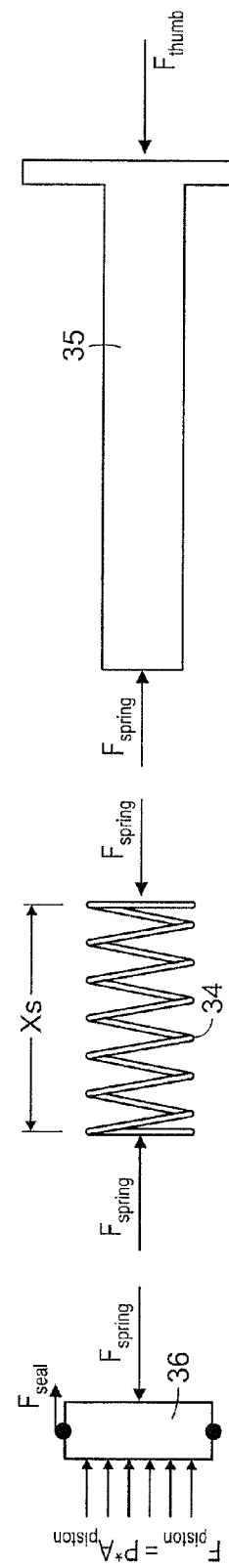
FIG. 3B is free body diagram of the components of FIG. 3A.

FIGS. 2A and 2B illustrate an advantage of certain embodiments of the present syringe, in particular when contrasted with FIGS. 3A and 3B, which are accurate functional depictions of the pressure-indicating syringe 30 shown in FIGS. 2 and 3 of U.S. Pat. No. 4,064,879 to Leibinsohn.

In the device of FIGS. 3A and 3B, the user applies an unknown force $F_{thumb}$ to the plunger 35. The plunger 35 pushes on the spring 34 and the spring pushes back with a force $F_{spring}$. At any point in the motion, the spring force $F_{spring}$ equals the product of the spring constant k with the difference between the free length of the spring $L_{spring}$ and the compressed length of the spring $X_s$.

However, this force $F_{spring}$, which can be accurately gauged by observing the change in length of the spring, does not accurately enable a determination of the pressure P. This is due to the fact that the spring force $F_{spring}$ pushes on the piston 36 and is resisted not only by the pressure force, $F_{piston}$, but also the seal force, $F_{seal}$. The seal force is a function of the pressure and the coefficient of friction between the seal material 32 and the outer barrel 31, and the initial preloading of the seal due to manufacturing tolerances. In addition, the coefficient of friction can vary due to humidity and temperature.

When operating with low fluid pressures, such as the relatively low pressures used in inflatable endotracheal cuffs, this variability in the seal force, $F_{seal}$, can affect the displacement of the spring mechanism, and thus render the pressure measurement inaccurate in the device of FIGS. 3A and 3B.

By contrast, as best illustrated in FIG. 2B, the present syringe 10 decouples the spring force of the bellows 14 from the seal force, $F_{seal}$, between the piston end 16 and the outer barrel 11. Thus, variations in the seal force will not impact the bellows displacement or the pressure measurement.

Accordingly the present invention solves the longfelt need to accurately measure low pressures by effectively directly coupling an elastic spring element to the pressure chamber by using a bellows that is free to expand due to the pressure in the chamber, yet is not constrained by any forces such as seal friction.

Accordingly, the spring (bellows 14) is coupled to the plunger 15 at a first (distal) portion of the spring, and a second (proximal) portion of the spring moves in response to fluid pressure within the syringe cavity 223. The first portion of the spring is mounted to the distal end of the plunger, and coupled to the plunger to form a sliding seal with an inner wall of the syringe. The second portion of the spring moves longitudinally within the syringe without sealing contact.

FIGS. 4A and 4B show a preferred embodiment of the plunger assembly 15 that operates in accordance with the embodiment of FIGS. 2A and 2B. The plunger assembly 15 can be assembled from two identical halves (15a, 15b) that can be joined together and adhered to one another using any suitable means, such as a mechanical connection, ultrasonic welding and/or a UV curable adhesive. For very high volumes, a single piece part can be injection molded. The assembled plunger 15 forms a cylindrical internal cavity that extends from an opening 19 at one end of the plunger 15 and is closed at the opposite end. The closed end of the plunger 15 includes a cap portion 55 that is adapted to enable the user to comfortably apply force to the end of the plunger 15. Near the cap portion 55 is an air vent hole 18a that vents the interior of the plunger to the atmosphere and ensures that the pressure measured by the bellows is in relation to the ambient atmosphere.

Figure 5A:
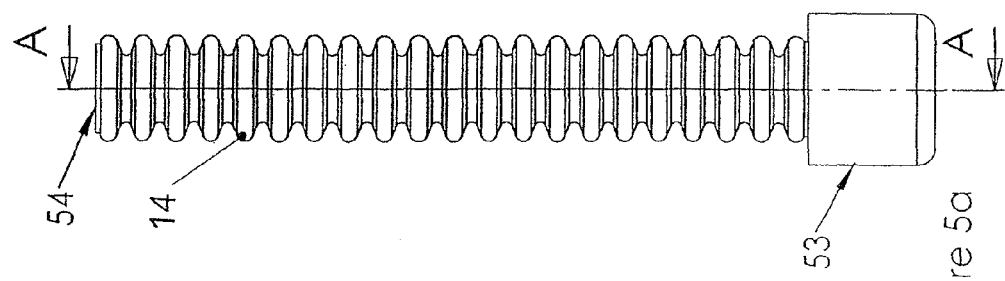
FIG. 5A is an isometric view of the preferred embodiment of the pressure sensing bellows.
Figure 5C:
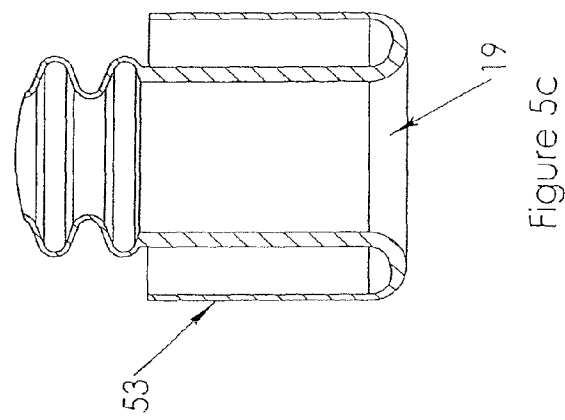
FIG. 5C is a close up view of one end of the preferred embodiment of the pressure sensing bellows.
Figure 5B:
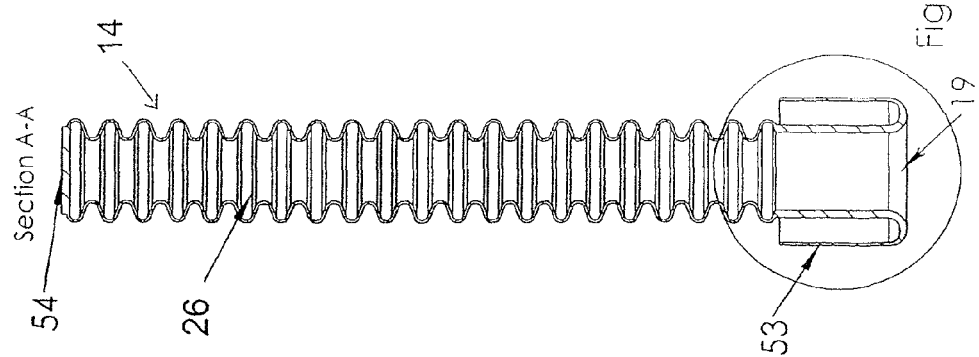
FIG. 5B is a cross section view of the preferred embodiment of the pressure sensing bellows.

FIGS. 5A-5C illustrate the bellows 14 according to one embodiment. The bellows 14 includes a tip 54 at one end of the bellows 14, and a hood 53 at the opposite end of the bellows 14. The bellows 14 is closed at the tip 54 and open proximate the hood 53. The hood 53 is fitted over the piston end 16 of the plunger 15, as is described in further detail below. In the assembled syringe, fluid enters the bellows 14 through opening 19 and fills the internal cavity 26, causing the bellows 14 to expand and contract as a function of the pressure. The piston 15 and the bellows 14 thus move relative to one another in a telescoping manner. The expansion and contraction of the bellows 14 causes the tip 54 to displace axially relative to the plunger 15 such that the position of the tip 54 relative to the pressure markings 42 gives a visual indication of the pressure to the clinician or caregiver.

As is shown in FIGS. 7A-7C, the hood 53 is placed over the piston end 16 of the plunger, and then O-rings 52a and 52b are placed over the hood which deforms the hood into the plunger grooves 50a and 50b causes the bellows to be anchored in place and an airtight seal to be maintained when the plunger 15 and bellows 14 assembly is placed into the outer barrel 11. A single O-ring and groove can typically provide adequate sealing, but here two are shown for added robustness. This configuration eliminates the need to use an adhesive or other bonding method for the assembly and sealing of the bellows to the plunger. Hence greater simplicity (lower cost) and greater reliability is achieved by the use of the hood and O-rings.

In one embodiment, the outside diameter of the plunger 15 is about 13 mm, the inside diameter is about 10 mm, and the inside diameter of a typical barrel 11 is 14 mm. To leave enough room for some plunger wall thickness, a soft upper limit for bellows outer diameter can be set at about 9 to 10 mm, and the inner diameter about 5 to 6 mm. The pitch of the bellows is typically 3 to 4 mm. Both rounded and triangular profile bellows can be used. If the device is used in the horizontal position, gravity will cause a drag force equal to the weight of the bellows and the coefficient of friction between the bellows material and the plunger plastic. The bellows weight will typically be about 2 grams with ½ of the weight "dragging" (the other end is supported by the piston), and the coefficient of friction at most 0.3: hence the drag force would be about 3 mN. The axial force on the bellows at the desired pressure of inflation will be about 60 mN. Hence the maximum expected error in pressure measurement will typically be about 5%. The tip 54 end of the bellows is thus mechanically decoupled from the wall of the plunger. Standard syringe plunger length also gave a soft upper limit on length of 50 to 75 mm. The bellows can have a wall thickness in a range of 0.1 to 1 mm, and can be around 0.5 mm, for example. With these parameters, the bellows material can be a soft elastomer (Shore 30-60A), such as a silicone rubber, to deform visibly at low pressure.

The bellows can be blow molded, which is likely the most inexpensive manufacturing option because of the re-entrant features; however, blow molding does not offer tolerances tighter than about ½ mm and also produces an inherent variation in wall thickness along the radius of the bellows. However, each bellows can be calibrated as it leaves the mold and be given a unique barcode. When it is assembled onto a plunger and placed in a barrel, a final laser marking for the pressure indication marks 42 can be made. Alternatively, after the system is assembled, pressure can be applied and the pressure indication marks can be laser marked as the pressure is increased and the position is measured, for example by a vision system. There are many manufacturers of suitable blow molded silicone elastomeric bellows, such as Albright Technologies in Leominster, Mass.

Tolerances for dip molding are even wider, with a minimum thickness of 1-2 mm. A high-precision injection molding process improves tolerances to 0.1 mm for parts in the critical size range are consequently used, but would require expensive tooling and thus would likely be appropriate for very high volume applications.

FIGS. 6A-6E show the plunger 15 with end cap 55 for the caregiver's thumb to apply a force to cause pressure to build up and flow into the cuff 23, and piston end 16. Piston end 16 contains seal grooves 50a and 50b and opening 19 for fluid pressure to enter into the bellows 18, which is placed inside the cylindrical internal cavity of the plunger 15, with the bellows hood 53 fit over the piston end 16.

FIGS. 6A-6C illustrate the pressure equalizing hole 18a that ensures the bellows will be subject to the pressure difference between the fluid in the cuff 23 and the ambient air. FIGS. 6A-6C also illustrate the pressure indicating marks 42.

FIG. 6C shows male and female alignment features (pin and hole) 64a and 64b on each of the plunger halves 15a, 15b. FIG. 6E shows similar alignment features 65a and 65b. When two identical plunger halves 15a, 15b are joined face-to-face, the male and female alignment features mate, so the plunger halves are aligned and a round plunger is obtained. The halves can be ultrasonically welded together, or a UV cure adhesive can be used. In high volumes, a monolithic design can be created.

FIGS. 7A-7C show a preferred embodiment of the syringe assembly 10 with the bellows 18 and plunger 15. Outer barrel 11 receives plunger 15, and a caregiver's thumb applies force to plunger end cap 55, and the reaction force from the caregiver's fingers can be received by flange 13. Pressurized fluid (e.g., air) flows through the syringe end 17 which can include a connection element (such as a Luer-lok portion) for forming a fluid-tight connection with an external fluid conduit that carries the pressurized fluid to the cuff 23 in FIG. 1.

FIGS. 8A and 8B illustrate yet another embodiment of a pressure-measuring syringe 800. The syringe 800 uses a bellows 806 as a spring and a seal inside the plunger 804, as shown in FIG. 8A. The rubber seal 810 (FIG. 8B) at the tip of the plunger 804 is used so that the syringe feels the same with a hole in the seal that couples the syringe air pressure to the bellows. The inside of the bellows is vented to the atmosphere at the base of the plunger. The bellows can be calibrated using a manometer and marks on the plunger in increments of 10 cm $H_2O$, for example.

This system works so that given 3 kPa of pressure, the bellows deflects by 42.7 mm, for example. A standard syringe outer shell (barrel) 802 of a 6 CC syringe 800 can be used, as shown in FIG. 8B. The system includes the bellows 806, the plunger tube 804 housing the bellows 806, the cap 808, and the seal 810 between the plunger 804 and the shell 802. To preserve the syringe feel, the existing rubber seal from the traditional plunger is used to seal the plunger to the shell, with the modification that a 0.075 inch hole is drilled through its axis to permit the air flow necessary to transmit pressure.

The bellows material can be, for example, soft rubber or plastic to deform visibly at low pressure. A commercial bellows, such as the product made by Blow Molded Specialties, can be used. The bellows dimensions for one embodiment are listed in Table 1. The bellows can be modified by adding another layer of similar-thickness rubber to the end to stiffen the tip and ensure that it does not deform, making the readout more difficult.

TABLE 1

Bellows Dimensions and Parameters

| Do | OJ | t | R | <p | Overall Length | Overall OO | Material |
|---|---|---|---|---|---|---|---|
| 0.35" | 0.27" | 0.010" | 0.020" | 18 deg | 2.62" | 0.355" | Neoprene: Shore 40A |

Figure 9:
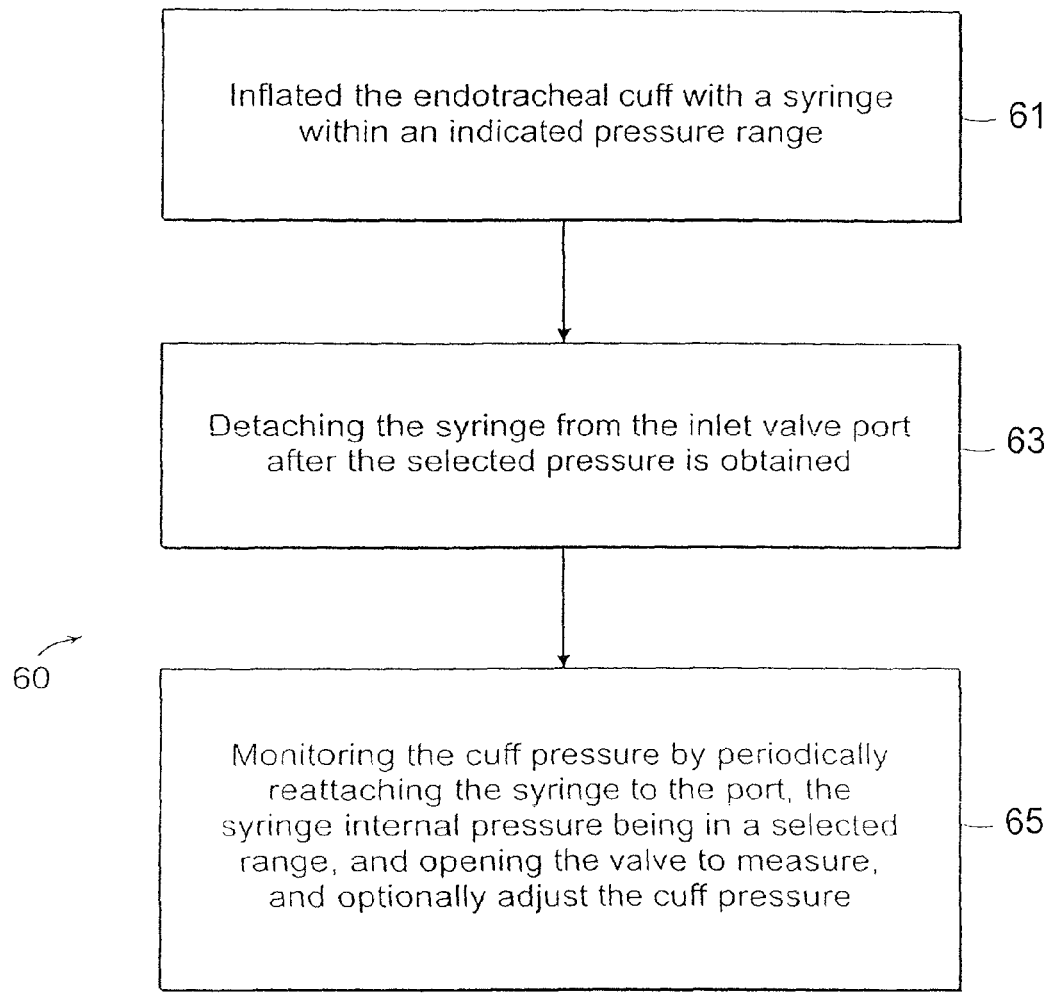
FIG. 9 illustrates a preferred method of monitoring endotracheal cuff pressure in accordance with the invention.

A process 60 for monitoring cuff pressure during a longer period of use is illustrated in the sequence of FIG. 9. This process includes initially inflating 61 the endotracheal cuff to a selected pressure with the syringe. The syringe is subsequently removed 63 as it is preferable not to have the syringe attached near the patients' mouth for long periods. To monitor the cuff pressure, the syringe can be periodically attached to the port with the syringe internal pressure being selected within the established range, such that the cuff pressure will not be significantly altered when the valve is opened to measure, and optionally adjust the cuff pressure 65.

Figure 10:
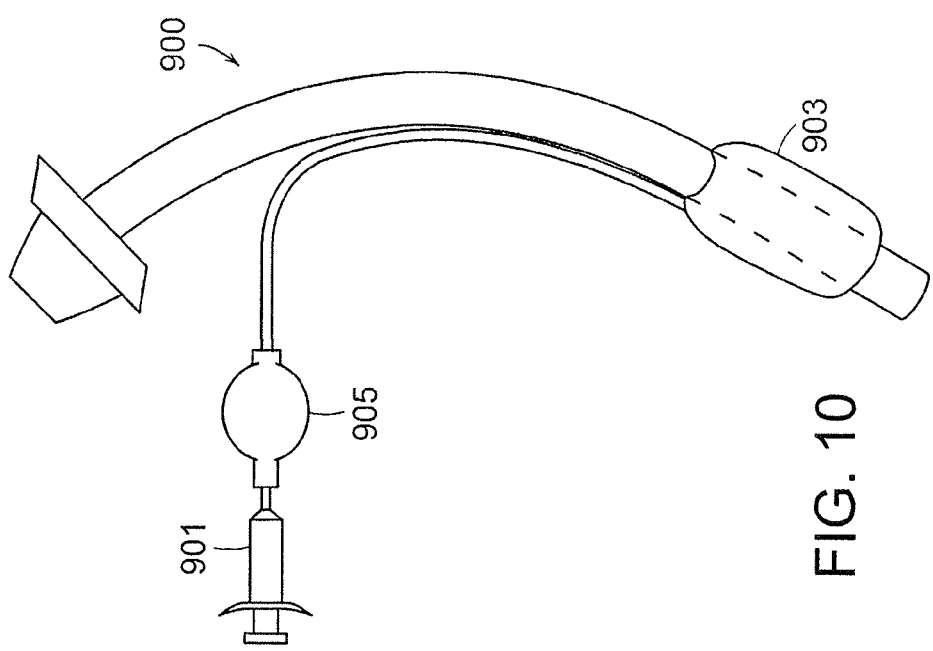
FIG. 10 illustrates a pediatric endotracheal tube assembly and a syringe with a pressure measuring device for inflating a cuff.

FIG. 10 illustrates a pediatric endotracheal tube (ETT) assembly 900 and a syringe 901 with a pressure-measuring gauge for inflating and/or measuring the pressure of a cuff. The syringe 901 attaches to an inlet valve 905 of the tube assembly 900 that is in fluid communication with the cuff 903, substantially as described above in connection with FIG. 1. Endotracheal tubes have been developed specifically for pediatric patients. These tubes are generally smaller and tailored for the anatomies of children. For example, the MICROCUFF Pediatric Endotracheal Tube from Kimberly-Clark, Inc. is sold in a variety of tube sizes, having interior tube diameters ranging from 3 mm (recommended for patients less than 8 months old) up to 7 mm (recommended for patients 14 to <16 years old). Furthermore, it is known that such pediatric tubes effectively seal at an average cuff pressure of 11 cm $H_2O$, or about half the pressure of conventional tubes. According to one embodiment, a syringe 801 of the present invention is calibrated to provide accurate pressure measurements of a pediatric endotracheal tube, and is sensitive over a range that includes pressures from at least about 0 to about 20 cm $H_2O$, or more particularly over a range from about 5 to about 15 cm $H_2O$. The pressure measurement device preferably comprises an internal bellows, substantially as described above, that is calibrated to accurately measure safe cuff pressures for a pediatric ETT. In certain embodiments, the syringe can be sensitive over a wide range of pressures, and can be used for both adult and pediatric ETT cuff pressure measurements. Separate markings can be provided on the syringe plunger to indicate safe pressure ranges for various types of cuffs. In other embodiments, application-specific pressure-measuring syringes, which are calibrated over specific pressure ranges are used to measure cuff pressure for specific devices having safe operating pressures falling within the respective syringe pressure-sensitivity ranges. A pediatric-specific syringe, for instance, could optionally be made smaller than a conventional syringe (e.g., 5 cc or less), and be sensitive over a range that includes pressures from at least about 0 to about 20 cm $H_2O$, or more particularly over a range from about 5 to about 15 cm $H_2O$.

Alternatively or in addition, application-specific pressure-measuring modules can be inserted into a syringe, wherein each module has a different pressure-measurement sensitivity range. The pressure measuring modules can be, for example, bellows having different bellows spring constants, that can be interchangeably used with a syringe, or interchangeable plunger assemblies, each with a different internal bellows and sensitive over a particular pressure range, that can be inserted into a reusable outer barrel. A set of differently-calibrated pressure-measuring syringes, or pressure-measuring modules for use with a syringe, can be provided as a kit.

Figure 11:
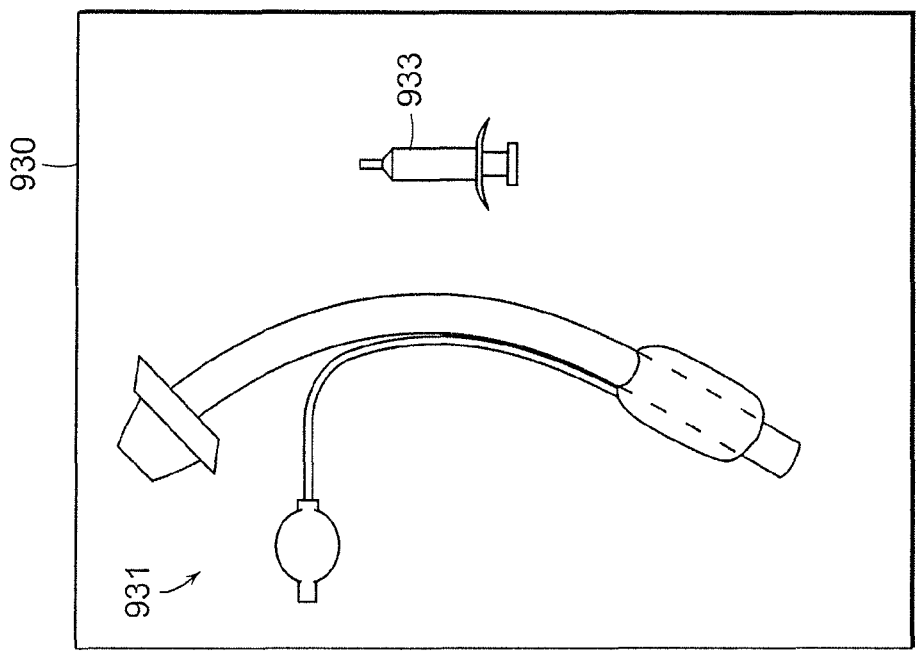
FIG. 11 illustrates a kit having an endotracheal tube assembly and a syringe with a pressure measuring device.

FIG. 11 illustrates a kit 930 comprising an endotracheal tube assembly 931 and a pressure-measuring syringe 933, that can be provided to enable a clinician to insert an endotracheal tube into a patient, inflate the cuff to a safe pressure, and accurately monitor and adjust the cuff pressure as needed over time. The tube assembly 931 and the syringe 933 can be sold together as disposable components. Alternatively, one or more components of the kit 930 can be autoclavable, for instance, and be reusable.

Although various embodiments of the present invention have been described in connection with a syringe for use with an endotracheal tube assembly, it will be understood that the present syringe with pressure measuring device can be used for other applications. For example, the present syringe can be used to inflate and measure the pressure in other inflatable medical devices, such as laryngeal masks, naso-tracheal tubes, larangeal-tubes, and the like. It will be understood that the pressure-measuring device, such as a bellows, can be calibrated to provide adequate pressure sensitivity over the safe operating range of the particular inflatable device. In the case of a laryngeal mask, for instance, the bellows spring can be calibrated to have a sensitivity at least over the safe operating pressure range of about 55 to about 60 cm $H_2O$.

Furthermore, in addition to use with inflatable medical devices, the present pressure-measuring syringe can be used in connection with any pressure-sensitive medical procedure, such as the injection of a liquid into a mammalian body, the injection of local anesthesia into nerves, and the diagnosis and treatment of compartment syndrome. A pressure measuring syringe for use in injection of anesthesia can have a bellows that is calibrated to be accurate at pressures up to around 100 cm $H_2O$, for example.

FIG. 12 illustrates a pressure-measuring syringe 940 used in a pressure-sensitive medical procedure on a patient 950. The syringe 940 can be used, for example, in the diagnosis and treatment of compartment syndrome. Compartment syndrome is characterized by an increased pressure in an enclosed anatomical space, and is typically found in spaces that are bound by inelastic fascia and bone and have a normal pressure that is less than 10 mm Hg (13.6 cm $H_2O$). The conventional diagnosis for compartment syndrome is made using a Striker needle, in which a needle is inserted in the compartment and a small amount of saline is injected, which reveals the pressure required to inject the saline. Typically, surgery (e.g., fasciotomy) is indicated for patients with pressure above 30 mm Hg (40.8 cm $H_2O$), and depending on other factors, may be indicated where the pressure is between 10 and 30 mm Hg (13.6-40.8 cm $H_2O$). A pressure-measuring syringe 940 of the present invention can be calibrated over these pressure ranges and can be used to detect compartment syndrome without using the expensive Stryker needle setup. This could also be useful for the military in crush injuries.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. A pressure measuring syringe comprising:
    a syringe barrel;
    a plunger extending within the barrel, the plunger having an internal cavity;
    a spring mounted within the internal cavity and coupled to the plunger at a first portion of the spring, the spring having a second portion that is movable in response to fluid pressure within a syringe cavity, the spring being fluidly coupled to the syringe cavity;
    a pressure indicator correlated to a plurality of positions of the second portion of the spring to visually indicate a fluid pressure within the syringe cavity.

2. The syringe of claim 1 wherein the second portion of the spring moves longitudinally within the plunger without sealing contact against an inner wall of the plunger.

3. The syringe of claim 1 wherein first portion of the spring is coupled to the plunger to form a sliding seal with an inner wall of the syringe barrel.

4. The syringe of claim 1 wherein the spring comprises a bellows that encloses fluid that flows relative to the syringe cavity.

5. The syringe of claim 1 wherein the pressure indicator comprises a plurality of at least three pressure levels of a fluid including at least a first level indicating under-inflation and at least a second level indicating over-inflation.

6. The syringe of claim 1 wherein the plunger has a distal end and a proximal end, the first portion of the spring being mounted to the distal end of the plunger.

7. The syringe of claim 1 wherein the spring has a distal end and a proximal end, the distal end having a fluid opening to the syringe cavity.

8. The syringe of claim 7 wherein the distal end of the spring comprises the first portion and the proximal end of the spring comprises the second portion.

9. The syringe of claim 8 wherein the proximal end of the spring has a visual indicator element that moves longitudinally relative to the piston to indicate fluid pressure.

10. The syringe of claim 1 wherein the fluid comprises a gas.

11. The syringe of claim 1 wherein the fluid comprises a liquid.

12. The syringe of claim 1 wherein the syringe is coupled to an endotracheal cuff to measure gas pressure in the cuff.

13. The syringe of claim 3 wherein the sliding seal comprises an o-ring.

14. The syringe of claim 1 wherein the spring comprises a coiled spring and/or flexible diaphragm.

15. The syringe of claim 1 wherein the syringe has a plurality of markers indicating a pressure range of at least 5 cm $H_2O$ to 35 cm $H_2O$.

16. The syringe of claim 1 wherein the plunger comprises a tubular body having an internal cavity in which the spring is positioned, the plunger having a distal opening to provide fluid coupling between that spring and a distal cavity of the syringe.

17. The syringe of claim 1 wherein a distal end of the spring is mechanically coupled to a distal end of the plunger.

18. The syringe of claim 1 wherein the syringe is coupled to a needle for injection of a liquid, such as saline, into a mammalian body.

19. The syringe of claim 1 wherein the syringe is coupled to a pediatric endotracheal tube.

20. An endotracheal cuff pressure measuring syringe comprising:
   a barrel having an aperture at a tip end for coupling to an endotracheal cuff and an opening at an opposed end;
   a plunger arranged within the barrel and forming a seal against an internal wall of the barrel to define a fluid chamber proximate the plunger;
   a bellows arranged within the plunger, the bellows mounted at a first end to the plunger to form a fluid seal and moveable at a second end to indicate a pressure within the fluid chamber; and
   visual indicia that indicate a plurality of different pressures within the fluid chamber based on a position of the bellows.

21. The syringe of claim 20 wherein plunger includes visual indicia indicate a high pressure limit and low-pressure limit within a range of 5 to 35 cm $H_2O$.

22. The syringe of claim 20 wherein the visual indicia indicate pressures within a range of 10 to 30 cm $H_2O$.

23. The syringe of claim 20 wherein the visual indicia are located on an outer wall surface of the plunger.

24. The syringe of claim 20 wherein the piston and the bellows move relative to one another in a telescoping manner.

25. The syringe of claim 23 wherein the bellows includes an internal cavity in fluid communication with the fluid chamber.

26. The syringe of claim 20 wherein the visual indicia comprise markings on the plunger that are visible as the plunger slides axially inside the syringe.

27. The syringe of claim 26 wherein the markings comprise graduated markings indicative of the fluid pressure in the chamber.

28. The syringe of claim 26 wherein the markings comprise variations in the coloration on the plunger.

29. The syringe of claim 5 further comprising an indicator on a proximal end of the bellows.

30. The syringe of claim 20 wherein the bellows has a wall thickness in a range of 0.1 to 1 mm.

31. The syringe of claim 20 wherein the visual indicia comprise a numeric pressure value.

32. The syringe of claim 20 wherein the bellows has a proximal end indicating either underpressure or overpressure in the cuff.

33. The syringe of claim 20 wherein the fluid chamber is in fluid communication with a cuff of an endotracheal tube, and the measured pressure comprises the pressure within the cuff.

34. The syringe of claim 27 wherein the markings include spaced apart markings indicating increments of pressure in a range of 1 to 5 cm $H_2O$.

35. A method of measuring the pressure within a cuff of an endotracheal tube comprising:
   coupling a syringe to an endotracheal tube cuff, the syringe comprising a barrel having an aperture at a tip end and having a plunger arranged within the barrel, the plunger forming a seal against an internal wall of the barrel to define a fluid chamber proximate the plunger, a spring positioned within the plunger and axially movable relative to the plunger, the spring mounted at a first portion to the plunger such that the axial movement of a second portion of the spring relative to the plunger is indicative of a pressure within the fluid chamber;
   actuating the syringe by depressing the plunger relative to the barrel; and
   measuring a gas pressure inside the endotracheal tube cuff using a position of the second portion of the spring.

36. The method of claim 35 further comprising viewing visual indicia that indicate the pressure within the fluid chamber based on the position of the spring, the visual indicia indicating pressures within a range of approximately 5 to 35 cm $H_2O$.

37. The method of claim 36 wherein the visual indicia further indicates pressure in a range of 10 to 30 cm $H_2O$.

38. The method of claim 35 wherein the step of measuring the pressure further comprises displacing a spring, the spring comprising a bellows that encloses a portion of the fluid chamber.

39. The method of claim 35 wherein the second end of the spring is mechanically decoupled from the wall of the plunger.

40. The method of claim 35 further comprising releasing manual pressure on the plunger and monitoring fluid pressure in the cuff with the syringe.

41. The method of claim 38 further comprising observing a position of an indicator element positioned on a proximal end of the bellows in relation to visual indicia on the plunger.

42. The method of claim 35 further comprising measuring under-inflation or over-inflation of the cuff.

43. The method of claim 35 wherein the actuating step further comprises inflating the cuff with the syringe.

44. The method of claim 43 wherein the step of inflating the cuff comprises manually pushing the plunger into the syringe barrel the plunger having a seal against an inner wall of the barrel that slides in a distal direction.

45. A method of fabricating a pressure measuring syringe comprising:
   inserting a spring into a cavity of a molded plastic plunger, the spring being coupled at a first portion to the plunger, the spring having a second portion that is longitudinally moveable relative to the plunger;
   inserting the plunger and spring into the syringe barrel to form a sealed fluid chamber within the syringe barrel such that the second portion of the spring visually indicates pressure.

46. The method of claim 45 wherein the spring comprises a molded bellows.

47. The method of claim 45 wherein the syringe barrel, and the spring are non-metallic.

48. The method of claim 45 further comprising forming markings on the plunger to indicate a plurality of pressure levels.

49. The method of claim 45 wherein the plunger comprises a piston at a distal end, a cap at the proximal end and an air vent.

50. The method of claim 45 wherein the syringe has a displaceable volume in a range of 2 to 20 cc.

* * * * *